United States Patent [19]

Schack et al.

[11] Patent Number: 4,578,225
[45] Date of Patent: Mar. 25, 1986

[54] MULTI-(OTEF$_5$)-SUBSTITUTED FLUOROCARBONS

[75] Inventors: Carl J. Schack, Chatsworth; Karl O. Christe, Calabasas, both of Calif.

[73] Assignee: The United States of America as represented by the Secretary of the Air Force, Washington, D.C.

[21] Appl. No.: 617,456

[22] Filed: May 29, 1984

[51] Int. Cl.$^4$ ............................................ C07C 165/00
[52] U.S. Cl. .................................. 260/550; 252/48.8
[58] Field of Search ........................................ 260/550

[56] References Cited

U.S. PATENT DOCUMENTS

| | | | |
|---|---|---|---|
| 4,258,208 | 3/1981 | Kao et al. | 260/550 |
| 4,307,259 | 12/1981 | Dittman | 570/125 |
| 4,508,662 | 4/1985 | Schack et al. | 260/550 |

OTHER PUBLICATIONS

Chemical Abstracts, vol. 95, 95:34545h.
M. Hobbs, Basics of Missile Guidance and Space Techniques, vol. I, pp. 1-81-1-89, (1959), Rider Publisher, Inc., N.Y.
K. Seppelt et al, Morganic Chemistry, vol. 12, No. 11 (1973), 2727-2730.
F. Sladky, Monatshefte für Chemie 101, 1559-70, 1571-1577 (1970).

Primary Examiner—Donald G. Daus
Assistant Examiner—Mary E. Ceperley
Attorney, Agent, or Firm—Donald J. Singer; Charles E. Bricker

[57] ABSTRACT

An acyclic compound of the formula $$C_nF_n(OTeF_5)_mX_p$$

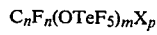

wherein X is F, H or Cl, n is an integer in the range of 2 to 6, m is an even integer in the range of 2 to n, and p is $(n-m+2)$.

Also provided is a cyclic compound of the formula $$C_aF_a(OTeF_5)_bX_c$$

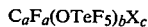

wherein X is F or Cl, a is 5 or 6, $C_a$ is a 5- or 6-membered ring, b is an integer having a value of 2 or 4 and c is $(a-b)$.

10 Claims, No Drawings

MULTI-(OTEF₅)-SUBSTITUTED FLUOROCARBONS

RIGHTS OF THE GOVERNMENT

The invention described herein may be manufactured and used by or for the Government of the United States for all governmental purposes without the payment of any royalty.

BACKGROUND OF THE INVENTION

This invention relates to high density fluorocarbon fluids.

High density fluids are desired for use in improved gyroscopes.

It is an object of the present invention to provide novel, high density, fluorocarbon fluids.

Other objects and aspects of the present invention will be apparent to those skilled in the art.

DESCRIPTION OF THE INVENTION

In accordance with the present invention there is provided an acyclic compound of the general formula $$C_nF_n(OTeF_5)_mX_p$$

wherein X is F, H or Cl, n is an integer in the range of 2 to 6, and m is an even integer in the range of 2 to n and p is (n−m+2). Also provided is a cyclic compound of the general formula $$C_aF_a(OTeF_5)_bX_c$$

wherein X is F or Cl, a is an integer having a value of 5 or 6, $C_a$ is a 5- or 6-membered ring, b is an integer having a value of 2 or 4, and c is an integer having a value of (a−b).

The compounds of the present invention are prepared by the reaction of Xenon bis-pentafluorotelluriumoxide, $Xe(OTeF_5)_2$, with a fluorinated olefin having at least one carbon-carbon double bond. The fluorinated olefin can be acyclic or cyclic with 5 or 6 carbon atoms in the ring. Examples of suitable fluorinated olefins include the following: tetrafluoroethylene, perfluoropropylene, trifluoroethylene, chlorotrifluoroethylene, 1,1-dichloro-2,2-difluoroethylene, hexafluoro-1,3-butadiene, perfluorocyclopentene, perfluorocyclohexene, perfluorodivinylethane, and the like.

The above reaction is carried out at a temperature in the approximate range of 50° to 150° C. above the atmospheric boiling point of the olefin, and at an elevated pressure which is approximately equal to the elevated vapor pressure of the olefin at the reaction temperature, for a time period in the approximate range of 10 to 150 hours. The reaction is preferably carried out in a closed system such as a sealed ampoule or other pressure reaction vessel. The compounds of the present invention may be recovered by fractional distillation.

The compounds of this invention are useful as gyroscopic fluids.

The following examples illustrate the invention.

GENERAL PROCEDURE

Volatile materials were manipulated in a stainless steel vacuum line equipped with Teflon FEP U-traps, 316 stainless steel bellows-seal valves, and a Heise Bourdon tube-type gauge. The synthetic reactions employed here were usually conducted in stainless steel cylinders. Infrared spectra were recorded on a Perkin Elmer Model 283 spectrophotometer using cells equipped with AgBr windows. Raman spectra were recorded at ambient temperature on a Cary Model 83 spectrophotometer with the use of the 488-nm exciting line of an Ar ion laser. Sealed Pyrex mp capillaries were used as sample containers. $^{19}F$ NMR spectra were recorded at 84.6 MHz on a Varian Model EM390 spectrometer with internal $CFCl_3$ as a standard with a negative chemical shift being upfield from $CFCl_3$.

EXAMPLE I

Synthesis of 1,2-Pentafluorotelluriumoxide Tetrafluoroethane

A 100 ml Teflon FEP ampoule was loaded with $Xe(OTeF_5)_2$ (2.66 mmol) in the glove box. From the vacuum line $C_2F_4$ (4.00 mmol) was condensed into the ampoule at −196° C. which was then warmed to ambient temperature for 2.5 days. At that point the volatile products were removed and separated by fractional condensation at −45° and −196° C. The low temperature trap contained mainly Xe(2.45 mmol) plus some $TeF_5OCF_2CF_3$ and a little $CF_3COF$. The material retained at −45° C. was a white solid which melted to a colorless liquid (mp −14° C.) with a vapor pressure of 5 mm at 0° C. and 17 mm at 20° C. It was identified as $(TeF_5O)_2C_2F_4$ on the basis of its vapor density molecular weight (g/mol; 573 Found, 577.2 calc.) and spectroscopic properties. Since white powdery $(C_2F_4)_n$ was also produced and remained in the ampoule it was not possible to determine by visual inspection if all the $Xe(OTeF_5)_2$ had reacted. Therefore, a second increment of $C_2F_4$(2.27 mmol) was added and allowed to react for 1 day as before. Nearly all the $C_2F_4$ was recovered but an additional 0.12 mmol of $(TeF_5O)_2C_2F_4$ was obtained. Overall, the yield of the bis-$TeF_5O$ compound was 82% (2.18 mmol) based on the limiting reagent, $Xe(OTeF_5)_2$.

EXAMPLE II

Synthesis of 1,2-Pentafluorotelluriumoxide Hexafluoropropane

A 30 ml stainless steel Hoke cylinder was loaded with $Xe(OTeF_5)_2$ (2.66 mmol) in the glove box. From the vacuum line $CF_3CF=CF_2$ (3.00 mmol) was condensed into the cylinder at −196° C. which was warmed to ambient temperature and then placed in an oven at 100° C. for 3 days. Separation of the products was accomplished by fractional condensation in a series of U-traps cooled at −30°, −78°, and −196° C. No residue remained behind in the cylinder. The trap cooled at −196° C. contained mainly Xe(2.8 mmol) plus some $CF_3CF=CF_2$ and a small amount of $R_fCOF$-type material. The −78° C. trap contained $TeF_5OCF_2CF_2CF_3$ and $TeF_5OCF(CF_3)_2$ (0.15 mmol total). Retained at −30° C. was a clear, colorless liquid (which remained liquid at −78° C.) with a vapor pressure of 3 mm at 0° C. and 11 mm at 20° C. This material was identified as $TeF_5OCF_2CF(OTeF_5)CF_3$ on the basis of the material balance of the reaction and its spectroscopic properties. The yield was 79% (2.10 mmol). During three weeks at ambient temperature no interaction of $Xe(OTeF_5)_2$ and $CF_3CF=CF_2$ was observable.

EXAMPLE III

Synthesis of 1,2-Pentafluorotelluriumoxide Perfluorocyclopentane

In the same manner as described for the preceding example, Xe(OTeF$_5$)$_2$ (2.94 mmol) and C$_5$F$_8$ (3.20 mmol) were reacted at 100° C. for 7 d. In addition to the desired product and unreacted C$_5$F$_8$, the main by-products consisted of Xe (3.1 mmol) and TeF$_5$OC$_5$F$_9$ (0.2 mmol). In the fractional condensation 1,2(TeF$_5$O)$_2$C$_5$F$_8$ was retained at −23° C. It was a colorless liquid with a vapor pressure of 2–3 mm at 20° C. and was further identified spectroscopically. The yield of the bis-TeF$_5$O compound was 71% (2.09 mmol). When this reaction was examined after 5 days at 100° C. the yield was 63% while in another experiment conducted at 60° C. for 5 days only about 4–5% reaction of the Xe(OTeF$_5$)$_2$ had occurred.

EXAMPLE IV

Other compounds prepared according to the previously described procedure are as follows:

| Compounds | Yield, % |
| --- | --- |
| TeF$_5$OCF$_2$CF(OTeF$_5$)CF(OTeF$_5$)CF$_2$OTeF$_5$ | 97 |
| TeF$_5$OCF$_2$CFCl(OTeF$_5$) | 81 |
| TeF$_5$OCF$_2$CCl$_2$(OTeF$_5$) | 60 |
| TeF$_5$OCF$_2$CFH(OTeF$_5$) | 71 |

Various modifications may be made to the present invention without departing from the spirit of the invention or the scope of the appended claims.

We claim:

1. A compound of the formula $$C_nF_n(OTeF_5)_mX_p$$

wherein X is F, H or Cl, n is an integer in the range of 2 to 6, m is an even integer in the range of 2 to n and p is (n−m+2).

2. In accordance with claim 1, the compound 1,2-pentafluorotelluriumoxide tetrafluoroethane.

3. In accordance with claim 1, the compound 1,2-pentafluorotelluriumoxide hexafluoropropane.

4. In accordance with claim 1, the compound 1,2,3,4-pentafluorotelluriumoxide hexafluorobutane.

5. In accordance with claim 1, the compound 1-chloro-1,2-pentafluorotelluriumoxide-1,2,2-trifluoroethane.

6. In accordance with claim 1, the compound 1,1-dichloro-2,2-difluoro-1,2-pentafluorotelluriumoxide ethane.

7. A compound of the formula $$C_aF_a(OTeF_5)_bX_c$$

wherein X is F or Cl, a is an integer having a value of 5 or 6, C$_a$ is a 5- or 6-membered ring, b is an integer having a value at 2 or 4, and c is an integer having a value of (a−b).

8. In accordance with claim 7, the compound 1,2-pentafluorotelluriumoxide perfluorocyclopentane.

9. A method for preparing an acyclic compound of the formula $$C_nF_n(OTeF_5)_mX_p$$

wherein X is F, H or Cl, n is an integer in the range of 2 to 6, m is an even integer in the range of 2 to n and p is (n−m+2), which comprises reacting xenon bis-pentafluorotellurium oxide with a fluorinated olefin having at least one double bond of the formula $$C_nF_nX_q$$

wherein X is F, H or Cl, n is an integer in the range of 2 to 6 and q is an integer in the range of 2 to n, at an elevated pressure at a temperature in the approximate range of 50° to 150° C. above the atmospheric boiling point of said olefin for a time period in the approximate range of 10 to 150 hours.

10. A method for preparing a cyclic compound of the formula $$C_aF_a(OTeF_5)_bX_c$$

wherein X if F or Cl, a is an integer having a value of 5 or 6, b is an integer having a value of 2 or 4, and c is an integer having a value of (a−b), which comprises reacting $$Xe(OTeF_5)_2$$

with a cyclic olefin having at least one double bond of the general formula $$C_aF_aX_d$$

wherein X is F or Cl, a is an integer as defined above, and d is an integer having a value of (a−2) or (a−4), at an elevated pressure at a temperature in the approximate range of 50° to 150° C. above the atmospheric boiling point of said olefin for a time period in the approximate range of 10 to 150 hours.

* * * * *